United States Patent [19]

Frickey et al.

[11] Patent Number: 5,028,528

[45] Date of Patent: Jul. 2, 1991

[54] ANALYTICAL ELEMENT FOR THEOPHYLLINE DETERMINATION USING BUFFER IN A SUBBING ZONE

[75] Inventors: Paul H. Frickey; Gary E. Norton, both of Rochester, N.Y.

[73] Assignee: Eastman Kodak Company, Rochester, N.Y.

[21] Appl. No.: 224,507

[22] Filed: Jul. 25, 1988

[51] Int. Cl.$^5$ .............................................. C12Q 1/42
[52] U.S. Cl. .................................... 435/21; 435/184; 435/805; 435/810; 436/825; 422/55; 422/56; 422/57
[58] Field of Search ................ 435/21, 184, 805, 810, 435/7.1, 7; 422/56, 55, 57; 436/825

[56] References Cited

U.S. PATENT DOCUMENTS

| | | | |
|---|---|---|---|
| 4,264,727 | 4/1981 | Kolehmainen et al. | 435/8 |
| 4,782,016 | 11/1988 | Norton | 435/7 |
| 4,782,017 | 11/1988 | Frickey et al. | 435/805 |
| 4,900,665 | 2/1990 | Terashima et al. | 435/805 |

OTHER PUBLICATIONS

Vinet et al., *Clin. Chem.*, 25:8, pp. 1370–1372 (1979).
Vinet et al., *Clin. Biochem.*, 11:2, pp. 57–61 (1978).
Fawaz et al., *Z. Physiol. Chem.*, 353, pp. 1779–1783 (1972).
Ansari et al., *Clinica Chimica Acta*, 118, pp. 135–139 (1982).
U.S. Ser. No. 692,473, Norton, filed Jan. 18, 1985.
U.S. Ser. No. 900,065, Frickey et al., filed Aug. 25, 1986.

*Primary Examiner*—Robert J. Warden
*Assistant Examiner*—Carol A. Spiegel
*Attorney, Agent, or Firm*—John R. Everett

[57] ABSTRACT

Theophylline can be determined with an analytical element and method which utilize the inhibition, by theophylline, of alkaline phosphatase activity on an appropriate substrate. The assay is carried out at a pH of 9 or less. The element comprises a porous spreading zone, a subbing zone and at least one other zone. The zones are in fluid contact with each other. The isoenzyme of alkaline phosphatase and a suitable substrate for the isoenzyme are located in different zones of the element. The subbing zone contains polyvinylpyrrolidone and a buffer for maintaining a pH of 9 or less.

9 Claims, No Drawings

ANALYTICAL ELEMENT FOR THEOPHYLLINE DETERMINATION USING BUFFER IN A SUBBING ZONE

FIELD OF THE INVENTION

The present invention relates to clinical chemistry and to dry analytical elements for the determination of theophylline in biological fluids.

BACKGROUND OF THE INVENTION

Theophylline is a drug frequently administered for treatment of asthma and pulmonary diseases. For the drug to be used successfully without serious side-effects, it must be frequently and carefully monitored in a patient because it has a relatively narrow therapeutic range of use, that is, 1–2 mg/dl.

Numerous techniques have been used to determine the amount of theophylline in human serum. Most of these techniques have serious drawbacks. For example, known spectrophotometric methods require large sample volumes, extensive pretreatment and suffer from interferences by similarly structured xanthines, such as caffeine and theobromine. Known gas chromatographic methods are more specific, but require derivatization and are time consuming.

Nonisotropic immunoassay techniques are most frequently used because they provide rapid results and are simple to use. Although satisfactory sensitivity has been generally obtained with immunoassay techniques, it has been found recently that they may produce highly elevated results depending upon a patient's renal condition and the specificity of the antibody used in the assay. Moreover, immunoassays require the use of generally costly reagents which have limited stability.

High performance liquid chromatography techniques are also known. These techniques vary in specificity depending upon whether pretreatment of the test sample is carried out. Organic extraction steps are necessary to improve the accuracy and specificity of the assay. Many chromatography methods are susceptible to interferences from a number of substances including some common antibiotics. Other disadvantages include the need for expensive instrumentation and a specialized technical staff to perform the assays.

It is known that theophylline can be determined by measuring its inhibitory effect on alkaline phosphatase activity. However, when assaying human biological fluids in this manner, it is known that endogenous alkaline phosphatase can affect the assay and render inaccurate results on the low side. Endogenous alkaline phosphatase must then be destroyed or removed in some manner prior to the assay to avoid this problem.

In commonly assigned U.S. Ser. No. 900,069, now U.S. Pat. No. 4,782,017, filed Aug. 25, 1986 by Frickey et al entitled "Analytical Element and Method for Theophylline Determination Using Buffer in Spreading Zone", an element is described that has an isoenzyme for alkaline phosphatase and a buffer for maintaining the pH at 9 or less during the assay. Substantially all of the buffer is located in the spreading layer. No buffer is included in the subbing layer of the element.

While this element provides a simple and rapid assay for theophylline in which endogenous alkaline phosphatase exhibits a reduced effect, there is a need for further improvement. The element described above has a limited range and significant alkaline phosphatase bias.

SUMMARY OF THE INVENTION

The problems noted above are ameliorated with a dry analytical element for the determination of theophylline comprising, in fluid contact, a porous spreading zone, a subbing zone and at least one additional zone, said element containing an isoenzyme of alkaline phosphatase that is capable of acting on a substrate for the isoenzyme at a pH of 9 or less, and a substrate for said isoenzyme, provided the phosphatase and substrate are in different zones of said element, and the subbing zone contains a polyvinylpyrrolidone and a buffer that is capable of maintaining the pH at 9 or less during the determination.

The present invention provides a simple and rapid assay for theophylline having all of the advantages of the element and assay described and claimed in copending U.S. Ser. No. 900,069, now U.S. Pat. No. 4,782,017 noted above. In addition, the element of the present invention has significantly improved range, alkaline phosphatase bias and stability.

These improvements were achieved unexpectedly by putting buffer and polyvinylpyrrolidone in the subbing zone of the element. Buffer may also be located in other zones of the element.

DETAILED DESCRIPTION OF THE INVENTION

The present invention relates to the determination of theophylline in biological fluids, and especially human biological fluids. As used herein, determination refers to either qualitative or quantitative measurements of the amount of theophylline in a test sample. In particular, this invention can be used to determine theophylline in human biological fluids which contain endogenous alkaline phosphatase (that is, naturally occurring enzyme) in any of its enzymatic forms (for example, liver, intestinal, placental or bone). For example, this invention can be advantageously used to assay sera, whole blood, plasma, spinal fluid, sputum, bile, saliva, and other biological fluids. It is also possible to use the invention to assay fluid preparations of tissue such as human skeletal muscle, kidney, placenta, heart, intestine, lung or other tissue. The preferred biological fluids used in the practice of this invention are human sera and whole blood.

Theophylline is determinable in the practice of this invention by inhibiting the activity of alkaline phosphatase, an enzyme which can act on a number of substrates to produce a detectable reaction product. For example, the following representative equation illustrates the production of a detectable dye by the action of alkaline phosphatase using a typical substrate, p-nitrophenyl phosphate:

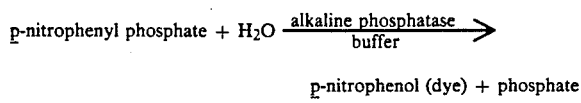

p-nitrophenol (dye) + phosphate

The dye can then be colorimetrically detected with suitable spectrophotometric detection equipment. The amount of theophylline present in the final reaction is inversely proportional to the amount of dye measured.

The present invention is practiced at a pH of 9 or less, and preferably at a pH of from 7 to 9. As noted in U.S. Ser. No. 692,473, now U.S. Pat. No. 4,782,016, noted above, endogenous alkaline phosphatase in human fluids has less activity at a pH of 9 or less. However, other isoenzymes of alkaline phosphatase which are not inactivated in an environment of pH 9 or less can also be used in the assay to indicate the presence of theophylline. Any isoenzyme from any suitable source which has that desired property, that is, activity measurable at a pH of 9 or less, is useful in the practice of this invention. Particularly useful isoenzymes are those obtained from bovine sources, for example tissues and organs (such as liver) of cattle or calves. Isoenzymes from various other sources (for example microorganisms, avian and nonhuman mammalian sources) are also useful. It is well within the skill of a worker in clinical chemistry to find isoenzymes which will be useful in the practice of this invention.

One or more of a variety of alkaline phosphatase substrates can be used in the practice of this invention. The substrate must be such that upon enzymatic reaction with the isoenzyme, a directly detectable change occurs. For example, the substrate is converted into one or more detectable reaction products, such as a chromogen, fluorogen, radioisotopically labeled species, and other suitable detectable products. The detectable change measured during the assay can be the appearance or disappearance of such a detectable product, or the change of one detectable product into another. Alternatively, the detectable change can be brought about through a series of reactions which are initiated by the action of the isoenzyme on the substrate. For example, the alkaline phosphatase isoenzyme can act on the substrate to release another enzyme or reagent which then is used in one or more reactions to produce a detectable product. The detectable product may be directly measurable, or require some physical separation or handling for measurement.

In a preferred embodiment of this invention, the assay provides a chromogen or fluorogen as a detectable product of the enzymatic reaction. Generally, the substrates which are useful in such reactions have a phosphate group which is cleaved from the substrate molecule during the enzymatic reaction. Such substrates include organic mono- or diesters of phosphoric acid or salts thereof. Examples of particularly useful substrates include p-nitrophenyl phosphate, phenolphthalein monophosphate, phenolphthalein diphosphate, thymolphthalein monophosphate, indoxyl phosphate, phenyl phosphate, $\alpha$-naphthol phosphate, $\beta$-naphthol phosphate, $\alpha$-glycerol phosphate, o-methylfluorescein phosphate, o-carboxyphenyl phosphate, alkali metal salts thereof and others known in the art, for example, in U.S. Pat. No. 3,425,912 (issued Feb. 4, 1969 to Deutsch et al) and European Patent Publication 61,731 (published Oct. 6, 1982). Preferred substrates are p-nitrophenyl phosphate and 4-(4-nitro-2-methylsulfonyl phenylazo)naphthol-1-phosphate.

The isoenzyme and substrate must be kept separated in different zones of the element until contacted with the liquid test sample. The amount of isoenzyme and substrate in the element can be varied widely. Generally, the element contains at least about 10 I.U./m$^2$ of the isoenzyme. In a preferred embodiment, the isoenzyme is present in a coverage of at least about 100 I.U./m$^2$, and more preferably, from about 125 to about 200 I.U./m$^2$. This embodiment is described and claimed in our copending and commonly assigned U.S. Ser. No. 900,068, filed on even date herewith and entitled "Improved Analytical Element and Method for Theophylline Determination Having Increased Alkaline Phosphatase Isoenzyme". In the context of this disclosure, I.U. represents the International Unit for isoenzyme activity defined as one I.U. being the amount of isoenzyme activity required to catalyze the conversion of 1 micromole of substrate per minute under standard pH and temperature conditions for the isoenzyme.

The substrate for the enzyme is generally present in an amount of from about 1 to about 5, and preferably from about 2 to about 4, g/m$^2$. Other addenda are incorporated into the element in amounts which are within the skill of an ordinary worker in clinical chemistry.

The assay is carried out at a pH of 9 or less, and preferably from about 7 to about 9. Any suitable buffer or mixture of buffers can be used in the practice of this invention as long as it is capable of maintaining the pH during the assay at 9 or less. Particularly useful buffers are nitrogen-containing organic buffers, many of which are standard in the art [for example, see Good et al, *Biochem*, 5(2), 1966, pp. 467–477]. Representative buffers include, but are not limited to, the group consisting of tris(hydroxymethyl)aminoethane.HCl, glycylglycine, N-tris(hydroxymethyl)-methyl-2-aminoethanesulfonic acid and N-2-hydroxyethylpiperazine-N'-2-ethanesulfonic acid. The first buffer is most preferred.

Buffer can also be located in the spreading zone and one or more other zones of the invention, as well as in the subbing zone. The buffer is present in the subbing zone in a suitable amount, depending upon the particular buffer, to maintain the pH of the reaction mixture at the desired pH of 9 or less. These buffering amounts can easily be determined by one of ordinary skill in clinical chemistry, but is generally at least about 1 g/m$^2$, and preferably at least about 2.5 g/m$^2$.

Other optional reagents can also be added to the element, if desired. For example, metal ion activators can be added to activate the isoenzymes. Such activators include divalent cations such as $Mg^{++}$, $Co^{++}$, $Mn^{++}$, $Ca^{++}$, $Zn^{++}$, $Sr^{++}$ and $Fe^{++}$, available in free or salt form (for example, aspartate, acetate, chloride or sulfate). Alternatively, if the levels of endogenous alkaline phosphatase in the test sample are abnormally high, inhibitors of the enzyme activity may be used. Useful inhibitors include phenylalanine and tetramisole. Such inhibitors advantageously do not affect the activity of some nonhuman alkaline phosphatase isoenzymes.

In addition, one or more phosphate acceptors are preferably included in the element to increase the rate of enzyme reaction when phosphate substrates are used. Useful phosphate acceptors include amino-alcohols or derivatives thereof, or aliphatic amines with the amino alcohols being particularly useful. Examples of such compounds are well known in the art.

Glycerol or another humectant can be added to one or more zones of the element in order to reduce element curl.

The element is divided into at least three zones including the subbing zone, the porous spreading zone and the isoenzyme and substrate are incorporated into individual zones. The zones can be separate layers, or finite areas within a single layer. They can be composed of the same or different materials and joined by lamination or other standard techniques.

The zones of the element can be self-supporting, that is composed of materials strong enough to maintain its integrity. Preferably, the zones are carried on a support. Such a support can be any suitable dimensionally stable, and preferably, transparent (that is, radiation transmissive) material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyesters, polycarbonates, cellulose esters, and others known in the art.

The subbing zone is prepared by adding isopropyl alcohol, a buffer, e.g. tris(hydroxymethyl)aminomethane.HCl, and polyvinyl pyrrolidone to a mill jar and milling the components for 72 hours at room temperature. It contains only the buffer and polyvinylpyrrolidone.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al). Alternatively, and preferably, the spreading zone is prepared from polymeric compositions (for example, blush polymers) or particulate materials, as described in U.S. Pat. Nos. 3,992,158 (issued Nov. 16, 1976 to Przybylowicz et al), 4,258,001 (issued Mar. 24, 1981 to Pierce et al), and 4,430,436 (issued Feb. 7, 1984 to Koyama et al) and Japanese Patent Publication 57(1982)-101760 (published June 24, 1982). It is desirable that the spreading zone be isotropically porous, meaning that the porosity is the same in each direction in the zone as caused by interconnected spaces or pores between particles, fibers or polymeric strands.

Most preferably, the porous spreading zone is prepared as a blush polymer layer as described in U.S. Pat. No. 3,992,158, noted above.

The elements have three essential zones as described above. The other zones which may be included in the element to good effect are a reagent zone or a registration zone as those zones are known in the art. The element can also have other zones including, but not limited to, additional spreading zones, radiation-blocking or radiation-filtering zones, other subbing zones or barrier zones. Preferably, all subbing zones are located between the two essential zones. Subbing zones help to insure that the isoenzyme and substrate do not interact prior to the assay. All zones in the element are generally in fluid contact with each other, meaning that fluids, reagents and reaction products (for example, color dyes) can pass or be transported between superposed regions of adjacent zones. Preferably, the zones are separately coated layers, although two or more zones can be a single layer. Besides the references noted above, suitable element components are described, for example, in U.S. Pat. Nos. 4,042,335 (issued Aug. 16, 1977 to Clément), 4,132,528 (issued Jan. 2, 1979 to Eikenberry et al) and 4,144,306 (issued Mar. 13, 1979 to Figueras).

A preferred embodiment of this invention is an element comprising a support having thereon, in order and in fluid contact, a layer containing the isoenzyme described herein, a radiation-blocking layer, a subbing layer containing the buffer and polyvinylpyrrolidone, and a porous spreading layer which contains a substrate for the isoenzyme and also the buffer. The isoenzyme layer can be a porous spreading layer also, but preferably, it is a reagent or registration layer containing one or more hydrophilic binders (for example, gelatin, vinyl pyrrolidone polymers or acrylamide polymers) surfactants, mordants, and other addenda. The subbing layer can comprise one or more subbing materials known to one skilled in the art, for example, vinyl pyrrolidone polymers, acrylamide polymers, and others known in the art. The radiation-blocking layer generally includes one or more binders, surfactants and reflective materials which are known in the art.

Optionally, this preferred element can also include a second porous spreading layer which is the outermost layer of the element, and which is generally contiguous to the first porous spreading layer. The second porous spreading layer can be constructed of materials the same as or different than those in the first porous spreading layer containing the isoenzyme substrate. For example, the first spreading layer containing the buffer can comprise blush polymers prepared according to U.S. Pat. No. 3,992,158, noted above, and the second spreading layer can be composed of particulate materials as described above. This second spreading layer can also contain buffer if desired.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, theophylline determination is made by taking the element from a supply roll, chip packet or other source and physically contacting it with a sample (for example, less than 200 μl) of the liquid to be tested. Such contact can be accomplished in any suitable manner, for example, by dipping or immersing the element into the sample or, preferably, by spotting the element by hand or machine with a drop of the sample with a suitable dispensing means.

After sample application, the element is exposed to any conditioning, such as incubation or heating, that may be desirable to quicken or otherwise facilitate obtaining any test result.

The alkaline phosphatase present in the element then catalyzes reaction of the substrate at a rate based on the amount of alkaline phosphatase present which is not inhibited by theophylline in the sample. The rate of detectable change (for example, dye formation) due to formation of the reaction product is quantifiable using suitable apparatus for reflection or transmission spectrophotometry. Suitable spectrophotometric apparatus and procedures are known in the art. Other suitable detection means include the use of fluorescence spectrophotometry, radiometry or enzyme labeling. The amount of theophylline is inversely proportional to the measured reaction rate.

For example, when p-nitrophenyl phosphate is used as the substrate, the uninhibited enzymatic reaction produces p-nitrophenol which is measurable at 400 nm using a standard spectrophotometer. The rate of the color change can then be directly related to the rate of substrate reaction which, in turn, is indirectly related to the concentration of theophylline in the sample.

In the following examples, which are provided to illustrate the practice of the invention, the materials used were obtained as follows:

Beef liver alkaline phosphatase isoenzyme, p-nitrophenyl phosphate and tris(hydroxymethyl)aminomethane.HCl buffer from Sigma Chemical Co. (St. Louis, Mo.), polyurethane resin as ESTANE from B.F. Goodrich (Cleveland, Ohio), BRIJ 78 surfactant from Ruger (Irvington, N.J.), DAXAD 30S surfactant from W. R. Grace (Lexington, Mass.), lyophilized albumin from Miles Laboratories, (Elkhart, Ind.), TRITON X-100, X-200E and X-405 surfactants from Rohm & Haas (Philadelphia, Pa.), and the remaining materials from Eastman Organic Chemicals (Rochester, N.Y.), or prepared using standard starting materials and procedures.

EXAMPLES

An element of this invention was prepared having the following format and components:

| | Element | Specific Amounts in Examples ($g/m^2$) | Range ($g/m^2$) |
|---|---|---|---|
| Spreading Layer | Titanium Dioxide | 39.5 | 20–50 |
| | Triton X-405 Surfactant | 1.7 | 0.1–10 |
| | Cellulose Acetate | 8.4 | 5–15 |
| | tris(hydroxymethyl)-aminomethane.Hcl (Tris) (pH 8) | 5.4 | 1–10 |
| | BRIJ 78 Surfactant | 0.8 | 0.1–3 |
| | p-Nitrophenyl Phosphate | 2.9 | 1–5 |
| Subbing Layer | Polyvinylpyrrolidone (PVP) | 0.8–3.3 | 0.5–5 |
| | tris(hydroxymethyl)-aminomethane (Tris) (pH 8) | 5.4 | 1–10 |
| Radiation-Blocking Layer | Gelatin (hardened) | 5.4 | 1–15 |
| | Piperazine-N,N'-bis-(2-hydroxypropane sulfonic acid) | 1.1 | 0.1–1 |
| | Titanium Dioxide | 32.2 | 20–50 |
| | TRITON X-200E | 0.1 | 0.1–3 |
| | Gelatin | 2.9 | 1–5 |
| | Glycerol | 1.1 | 1–3 |
| | DAXAD 30S surfactant | 0.2 | 0.1–1 |
| | BVSME gel hardener | 0.18 | 0.1–1 |
| | POPSO | 0.5 | 1–2 |
| Registration Layer | Gelatin (hardened) | 10.9 | 2–20 |
| | Piperazine-N,N'-bis-(2-hydroxypropane sulfonic acid) | 1.1 | 0.5–5 |
| | Magnesium chloride | 0.03 | 0.005–0.1 |
| | TRITON X-100 surfactant | 1.1 | 0.1–2 |
| | Poly(styrene-co-N-vinyl-benzyl-N-benzyl-N,N-dimethylammonium chloride-co-divinyl-benzene) | 1.1 | 0.5–1.5 |
| | Bovine Serum Albumin | 1.14 | 0.1–2 |
| | Glycerol | 1.1 | 0.1–2.5 |
| | Alkaline phosphatase beef liver enzyme | 156 | 60–200 I.U./$m^2$ |
| | Polyester Support | | |

A Control element similar to that described in U.S. Ser. No. 900,069, now U.S. Pat. No. 4,782,017, noted above, except for the levels of buffer and alkaline phosphatase isoenzyme was prepared which included buffer in the spreading layer.

The rate range and alkaline phosphatase bias of the assay was evaluated by spotting serum containing various levels of theophylline (up to 40 μg/ml) on the elements and measuring the reflection densities over a seven minute period using a rate analyzer. The results are shown in Table I below. A larger range is indicative of greater sensitivity in theophylline determination. The elements of this invention exhibit a statistically significant increase in range over the Control elements.

TABLE I

Range, Rate and % Inhibition

| | $mg/ft^2$ | | | | | | | |
|---|---|---|---|---|---|---|---|---|
| | PVP in | Tris in | | ΔD/min | | ΔD/min | | |
| Coating # | Subbing Layer | Subbing Layer | Spreading Layer | @0.9 μg/mL Theo | − | @37.5 μg/mL Theo | = Range | % Inhib. | Alk Phos Bias |
| 1 | 300 | 500 | 0 | 0.3271 | − | 0.14099 | = 0.18622 | 57 | −1.37 |
| 2 | 200 | 500 | 0 | 0.32637 | − | 0.13911 | = 0.18726 | 57 | −1.18 |
| 3 | 100 | 500 | 0 | 0.30293 | − | 0.12543 | = 0.1775 | 59 | −0.78 |
| Control | 75 | 0 | 500 | 0.28765 | − | 0.11862 | = 0.16903 | 59 | −1.42 |

Rate window 60–120 sec
λ = 400 nm

EXPERIMENTAL

Transfer of Tris [Tris(hydroxymethyl)-amino methanol (Tris) from Spreading Layer (SL) to Subbing Layer Advantages of placing Tris in subbing in comparison to spreading layer:

Increased range - When Tris was coated in the subbing layer instead of the SL, the range of the coatings increased from 5 to 10%, depending on the level of PVP in the 03 layer (Table I). When the level of PVP in the sub layer was decreased to 100 mg/ft, the range of the coating decreased to about 5% of the control coating. The range of the coating increased 10% over the control when the level of PVP was increased to 300 mg/ft.

Alkaline Phosphatase Bias - Paired fluids were spiked with 18.5 g/mL of theophylline and, in addition, one of the fluids was also spiked with 1000 U/mL of alkaline phosphatase. When these fluids were spotted on theophylline coatings with Tris and varying levels of PVP in the subbing layer, the alkaline phosphatase bias decreased with decreasing amount of PVP (Table I). The maximum decrease (43%) was observed in coating which contained 100 mg/ft of PVP and 500 mg/ft of Tris in the subbing layer.

Improved Keeping

All coatings were held for two weeks at 25° C. with the humidity adjusted to either 15 or 50%. The mean bias of the predicted theophylline concentration was determined by comparing responses of the above coatings to similar coatings which were held at 26° C. In general, the bias decreased with decreasing concentration of PVP and a fixed concentration of Tris in the subbing layer for each temperature-humidity combination in comparison to the control coating with Tris only in the smoothing layer. Furthermore, the biases were lower at the lower humidty (15%) levels. Coating with Tris and PVP in subbing layer had the lowest biases at either humidty level (Tables II and III) in comparison to the control coating.

TABLE II

| | mg/ft² | | | Keeping Conditions | Mean Bias from Predicted Theophylline Concentrations | | |
|---|---|---|---|---|---|---|---|
| | PVP in | Tris in | | 1-Week Keeping Temp (°C.) | Theophylline Conc. of Calibrator (μg/mL) | | |
| Coating # | Subbing Layer | Subbing Layer | Spreading Layer | RH (%) 1 Week @ | 0.9 | 9.5 | 37.5 |
| 1 | 300 | 500 | 0 | 25/15 | −0.04 | −0.54 | −2.68 |
| | | | | 25/50 | −0.06 | −3.25 | −10.09 |
| 2 | 200 | 500 | 0 | 25/15 | ND | ND | ND |
| | | | | 25/50 | 0.01 | −3.01 | −7.24 |
| 3 | 100 | 500 | 0 | 25/15 | 0.17 | 0.97 | −1.19 |
| | | | | 25/50 | 0.24 | −0.90 | −6.23 |
| Control | 75 | 0 | 500 | 25/15 | ND | ND | ND |
| | | | | 25/50 | 0.34 | −2.05 | −7.62 |

Rate window 60–120 sec
λ = 400 nm

TABLE III

| | mg/ft² | | | Keeping Conditions | Mean Bias from Predicted Theophylline Concentrations | | |
|---|---|---|---|---|---|---|---|
| | PVP in | Tris in | | 2-Week Keeping Temp (°C.) | Theophylline Conc. of Calibrator (μg/mL) | | |
| Coating # | Subbing Layer | Subbing Layer | Spreading Layer | RH (%) 2 Week @ | 0.9 | 9.5 | 37.5 |
| 1 | 300 | 500 | 10 | 25/15 | −0.24 | −1.71 | −4.51 |
| | | | | 25/50 | −0.09 | −4.25 | −15.39 |
| 2 | 200 | 500 | 0 | 25/15 | 0.05 | 0.95 | −3.71 |
| | | | | 25/50 | 0.23 | −2.95 | −14.00 |
| 3 | 100 | 500 | 0 | 25/15 | 0.04 | 0.53 | −3.59 |
| | | | | 25/50 | 0.01 | −2.61 | −8.03 |
| Control | 75 | 0 | 500 | 25/15 | −0.05 | −1.39 | −8.92 |
| | | | | 25/50 | 0.13 | −3.61 | −13.57 |

Rate window 60–120 sec
λ = 400 nm

The invention has been described in detail with particular reference to preferred embodiments thereof, but it will be understood that variations and modifications can be effected within the spirit and scope of the invention.

We claim:

1. A dry analytical element for the determination of theophylline comprising, in fluid contact, a porous spreading zone, a subbing zone and at least one additional zone, said element containing an isoenzyme of alkaline phosphatase that is capable of acting on a substrate for the isoenzyme at a pH between about 7 to 9, and a substrate for said isoenzyme, provided the phosphatase and substrate are in different zones of said element, and the subbing zone contains a polyvinylpyrrolidone and a buffer that is capable of maintaining the pH between about 7 to 9 and wherein the buffer is selected from the group consisting of tris(hydroxymethyl)aminomethane.HCl, glycylglycine, N-tris(hydroxymethyl)-methyl-2-aminoethanesulfonic acid and N-2-hydroxyethylpiperazine-N'-2-ethanesulfonic acid.

2. The element of claim 1 wherein the phosphatase substrate is in the spreading zone.

3. The element of claim 1 wherein the substrate is an organic mono- or diester of phosphoric acid and said phosphatase isoenzyme is bovine liver alkaline phosphatase.

4. The element of claim 1 wherein the subbing zone comprises 5.4 g/M² of buffer and 0.8 to 3.3 g/M² of polyvinylpyrrolidone.

5. The element of claim 1 wherein buffer is also included in the spreading zone and/or at least one other zone.

6. An analytical element for the determination of theophylline comprising: a support having thereon, in order and in fluid contact:
 (a) porous spreading layer, a substrate for an isoenzyme of alkaline phosphatase and a buffer that is capable of acting on the substrate at a pH of about 7 to 9;
 (b) a subbing layer containing polyvinylpyrrolidone and buffer that is capable of maintaining the pH of about 7 to at 9 during the determination and the buffer is selected from the group consisting of tris(-hydroxymethyl)aminomethane.HCl, glycylglycine, N-tris(hydroxymethyl)-methyl-2-aminoethanesulfonic acid and N-2-hydroxyethylpiperazine-N'-2-ethanesulfonic acid;
 (c) a reagent layer containing an isoenzyme of alkaline phosphatase that is capable of acting on a substrate for the isoenzyme at a pH of about 7 to 9; and
 (d) radiation-blocking layer.

7. The element of claim 6 wherein the porous spreading layer comprises titanium dioxide.

8. The element of claim 6 wherein the substrate is selected from the group consisting of p-nitrophenyl phosphate and 4-(4-nitro-2-methylsulfonyl phenylazo)-naphthol-1-phosphate, the alkaline phosphatase is bovine liver alkaline phosphatase, and the buffer is selected from the group consisting of tris(hydroxymethyl)aminomethane.HCl, glycylglycine, N-tris(hydroxymethyl)-methyl-2-aminoethanesulfonic acid and N-2-hydroxyethylpiperazine-N'-2-ethanesulfonic acid.

9. The element of claim 8 wherein the substrate is p-nitrophenyl phosphate and the subbing layer comprises 5.4 g/M² of tris(hydroxymethyl)aminomethane.HCl and 0.8 to 3.3 g/M² of polyvinylpyrrolidone.

* * * * *